United States Patent [19]

Shippert

[11] 4,153,051
[45] May 8, 1979

[54] COMPOUND SPLINT AND KIT

[76] Inventor: Ronald D. Shippert, 6260 S. Ivy St., Englewood, Colo. 80110

[21] Appl. No.: 813,800

[22] Filed: Jul. 8, 1977

[51] Int. Cl.² .................................... A61F 5/04
[52] U.S. Cl. ........................ 128/89 R; 128/76 C
[58] Field of Search .............. 128/76 C, 89 R, 87, 128/163, 132, DIG. 15

[56] References Cited

U.S. PATENT DOCUMENTS

| 3,742,943 | 7/1973 | Malmin | 128/76 C |
| 3,835,848 | 9/1974 | Berner | 128/76 C |

FOREIGN PATENT DOCUMENTS 437661  12/1925  Fed. Rep. of Germany ........ 128/76 C

OTHER PUBLICATIONS

Alumafoam Nasal Splint, Conco Catalogue, p. 12, Oct. 1972.

*Primary Examiner*—John D. Yasko
*Attorney, Agent, or Firm*—Sheridan, Ross, Fields & McIntosh

[57] ABSTRACT

A compound splint, primarily for use after nasal surgery, prevents edema fluid from splaying the bones apart so that they will grow back together and includes a base layer of adhesive tape applied directly to the nose, a secondary component of flexible material adhesively secured to the base layer and having a multiple loop formation on its outer face, and a primary restraining component. The latter includes a panel of malleable metal and a layer of fabric secured to one face of the panel, the fabric having a multiple hook formation. In use, the primary component is applied to the central portion of the secondary component, engaging some of the hooks and loops. The side portions are then pressed inwardly against the sides of the nose to the desired final shape, engaging the balance of the hooks and loops. Thus the primary component is securely anchored in place and prevents any change in size or shape of the traumatized nose during recovery.

12 Claims, 5 Drawing Figures

U.S. Patent  May 8, 1979  4,153,051
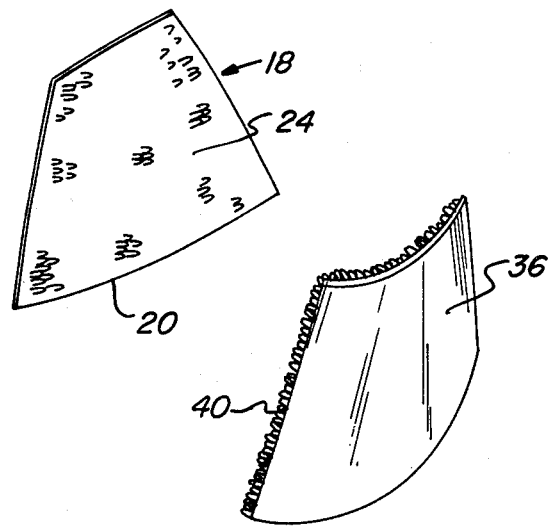
Fig-1
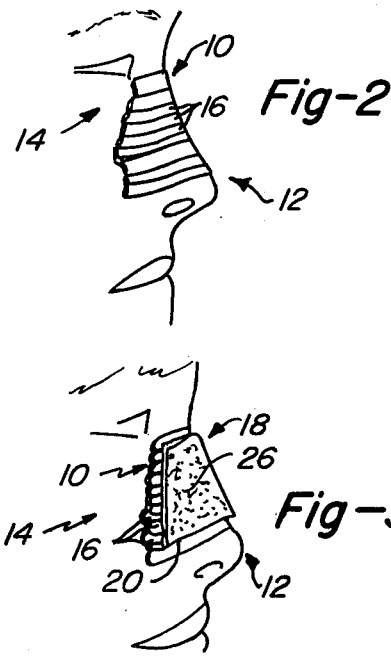
Fig-2
Fig-3
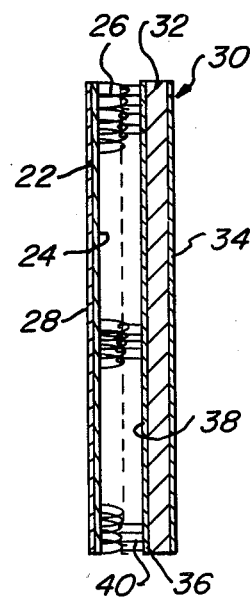
Fig-5
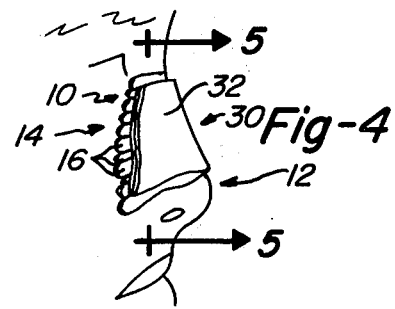
Fig-4

COMPOUND SPLINT AND KIT

BACKGROUND OF THE INVENTION

The device of this invention lies in the field of splints or braces for application to traumatized portions of a human body and is directed more particularly to a device of this class which is useful in maintaining during the healing period a traumatized nose resulting from injury or surgery in the desired size and shape after squeezing out all of the edema fluid from the soft tissue.

For many years it has been common practice to form splints from Plaster of Paris for use in maintaining immobility of bony segments after surgery. They are difficult to make and difficult to retain in place, requiring excessive taping or bandaging, in addition to being uncomfortable and unsightly. Various other approaches have been tried with indifferent success.

One approach has been the molding of a complete face mask, the nose portion of which is then modified to the desired contour. One or more blanks of sheet material are then formed to fit the contour and secured to a restraining member. The device is placed over the nose and an elastic band connected to the ends of the restraining member is passed around the back of the head to hold the splint in place. An example of this type is disclosed in U.S. Pat. No. 3,742,943 to Malmin. Obviously the method is expensive and time consuming, and the splint is easily displaced from its intended position.

In a somewhat similar approach a piece of malleable sheet metal of about the same area as the nose is laid against the nose and then pressed inward to assume the same shape as the nose. A retainer similar to a pair of goggles is applied to the splint and a headband connected to the ends of the retainer tends to hold it in place. An example of this type is disclosed in U.S. Pat. No. 3,835,848 to Berner. While the method of manufacture is simpler and cheaper than that of Malmin, it suffers from the same disadvantages in use. The device is uncomfortable and unsightly and the splint itself is easily displaced especially when the wearer is sleeping. Since neither of these devices is directly secured to the nose they both fail to maintain constant pressure on precise areas to prevent swelling or distortion.

SUMMARY OF THE INVENTION

The device of this invention and its method of application overcome the difficulties and disadvantages mentioned above and provide a compound splint which is inexpensive in materials, easy to apply and form to the desired shape, and firmly anchored in position to perform its proper function.

Generally stated, the total compound splint includes a base layer, a secondary component, and a primary restraining component. The base layer may be a single piece of adhesive tape but preferably consists of a plurality of narrow strips of tape laid across the nose laterally with each successive strip overlapping the preceding one in the longitudinal direction and firmly pressed in place. The secondary component is preferably a layer of flexible material such as woven fabric with a first face adapted to engage the tape and a second face provided with a multiple loop, hook-receiving, formation. Either the first face of the secondary component or the exposed face of the base layer is provided with an adhesive coating, and the secondary component is pressed into secured relation with the base layer.

The primary component includes a malleable metallic panel and a soft flexible layer, preferably of woven fabric, formed on a first face with a multiple hook formation. The second face is adhesively secured to the metallic panel. To complete the installation of the splint the primary component is placed in contact with the secondary component with the central portion of the hook formation engaging the central portion of the loop formation. The primary component is then pressed inwardly against the two sides of the nose covering the remaining hooks engage the loop formation and causing the edema fluid to be squeezed out of the soft tissue above the bones. When the panel is bent to a shape corresponding to that of the nose, substantially all of the hooks are engaged with the loops and the panel is in position to firmly retain the nose in desired shape during recovery. Any swelling which takes place will now occur inwardly rather than outwardly due to the pressure of the splint so that the bones which are to knit together cannot be splayed.

BRIEF DESCRIPTION OF THE DRAWINGS

Various other advantages and features of novelty will become apparent as the description proceeds in conjunction with the accompanying drawings, in which:

FIG. 1 is a perspective view of the hook and loop segments with their mating faces confronting each other;

FIG. 2 is a fragmentary side elevational view of a person's head with the base layer in position;

FIG. 3 is a view similar to FIG. 2 with the secondary component in position;

FIG. 4 is a view similar to FIG. 3 with the primary component in position; and

FIG. 5 is a greatly enlarged sectional view taken on line 5—5 of FIG. 4.

DESCRIPTION OF THE PREFERRED EMBODIMENTS

The compound splint and its application are schematically illustrated in FIGS. 2 and 4, in which a base layer 10 is shown in position on the nose 12 of the person 14. The base layer, in preferred form, is produced by sequentially applying a plurality of strips 16 of adhesive tape, preferably paper, to the nose laterally, starting near the radix end with each successive strip overlapping the preceding strip in a longitudinal direction to the dome end, the strips extending to or slightly beyond the lateral osteotomy sites. The skin is first cleansed and dried, and then a coating of tincture of benzoin or the like is applied and also allowed to dry thoroughly before the tape is applied.

A secondary component 18 is shown in FIGS. 1 and 5 as being in the form of a thin flexible layer 20 of material such as woven fabric having a first face 22 adapted to be applied to the base layer and a second face 24 provided with a multiple loop, hook-receiving, formation 26 which serves a dual purpose as a connector means and as a felt-like body having sufficient thickness to produce a cushioning effect. The first face is adapted to be adhesively secured to the base layer. The latter may have an adhesive coating but it is presently preferred to provide the adhesive coating on face 22 and protect it with a release sheet 28 until it is to be used. Component 18 is trimmed to a shape corresponding to that of the base layer but of less lateral and longitudinal extent so that when applied it will not extend laterally beyond the lateral osteotomy sites. The release sheet is stripped off and face 22 is pressed tightly against the base layer to be fixedly united thereto, as shown in FIG. 3.

The primary restraining component 30 is shown in FIG. 5 as being made up of a malleable metallic panel 32 having a coating of flesh-colored tape 34 on its exposed side and adhesively united on its second side to a layer 36 of flexible fabric provided on its exposed face 38 with a multiple hook formation 40. Layers 20 and 36 with their loop and hook connector means are available on the market and are sold under several brand names including the trademark VELCRO. Component 30 is trimmed to have almost identically the same planform as component 18, being a few millimeters larger laterally and longitudinally to overlie the edges of component 18. Panel 32 is preferably made from a sheet of soft aluminum having a thickness of the order of sixteen gauge.

Component 30, in its flat form, is applied to panel 18 in such fashion that the vertically central portion of layer 37 contacts the vertically central portion of layer 20, and some of the hooks engage some of the loops. The side portions of component 30 are then gently but firmly pressed inward toward the sides of the nose until it assumes the same shape, with the remainder of the hooks engaging the loops progressively until all of component 30 is securely fashioned in place. As component 30 is pressed into place, the edema fluid will be squeezed from the soft tissue above the bony structure of the nose. Although panel 32 is malleable enough to be formed manually it is adequately stiff enough to prevent any outward swelling or distortion of the nose during the recovery period, which would splay the bones before they begin to knit together. Thus, any swelling which occurs will be inward and therefore will not affect the healing process.

It will be apparent that the principal components may be prepared, stocked, and sold in kit form in which the malleable panel 32, the hook formation layer 36, and the loop formation layer 20 are cut to a trapezoidal planform as shown. In such kit, layer 36 is already secured to one face of panel 32 and the flesh colored tape 34 is secured to its other face. Layer 20 has an adhesive coating covered with release sheet 28. The hook and loop formations are pressed together as shown in FIG. 5 to produce a simple and neat package which remains in its flat form until it is to be used. At that time the hook and loop formations are separated, the release sheet is stripped off, and the secondary component is ready to be mounted in position. The tape strips are readily available in any medical office or hospital and need not be supplied with the kit. In some cases the tape is not used, and layer 20 may be applied directly to the skin. The trapezoidal shape conforms to the area of the nose to be covered and may be supplied in a variety of sizes to that special trimming will seldom be necessary.

The splint is of minimum size and has a flesh-colored exterior so that it has a minimum deleterious effect on the appearance. It is firmly secured so that it will not be displaced in ordinary activity including bathing and sleeping. Most importantly, its rigidity and secure mounting insure that it will perform its intended function properly and reliably.

The invention has been described in detail with particular reference to the preferred embodiment thereof, but it will be understood that variations and modifications can be effected within the spirit and scope of the invention.

What is claimed is:

1. A compound splint for application to a traumatized portion of a human body, including bones to be knitted together, a base layer of thin flexible material coated with adhesive on at least one side and adapted to be adhesively secured to the traumatized portion, said splint comprising:
   a secondary component in the form of a layer of flexible material of less area than the base layer having a first face adapted to be adhesively secured to the base layer and a second face provided with a multiple loop, hook-receiving formation;
   and a primary restraining component of malleable metallic material having a planform substantially identical to the planform of the secondary component and provided on one face with a multiple hook formation to anchoringly engage the multiple loop formation of the secondary layer;
   the primary restraining component being manually formable in situ to correspond to the shape of the traumatized portion and securable in place by the hook and loop formations to prevent change in the size and shape of the traumatized portion during recovery.

2. A splint as claimed in claim 1 further including the base layer wherein the base layer comprises:
   a plurality of laterally extending longitudinally overlapping strips of adhesive tape.

3. A splint as claimed in claim 1 in which:
   the secondary component comprises a thin layer of fabric having an adhesive coating on its first face; and
   the multiple loop formation on the second face comprises a felt-like material having sufficient thickness to produce a cushioning effect.

4. A splint as claimed in claim 1 in which:
   the primary component comprises a panel of malleable metal and a layer of fabric adhesively secured to one face of the panel, the fabric layer being provided with a multiplicity of hooks to anchoringly engage the multiple loop formation.

5. A splint as claimed in claim 4 in which:
   the panel is formed from a sheet of soft aluminum having a thickness of the order of sixteen gauge.

6. A method of forming and applying a splint to the traumatized nose of a human being, comprising:
   adhesively applying to the nose a base layer of thin flexible material;
   forming a secondary component of thin flexible material having a multiple loop formation on a second face to a shape corresponding to that of the base layer and smaller in area;
   adhesively applying the first face of the secondary component to the exposed face of the base layer;
   forming a malleable panel and a fabric layer having a multiple hook formation on its first face to a planform substantially identical to that of the secondary component;
   adhesively securing the second face of the fabric layer to one face of the malleable panel to form a laminated primary restraining component;
   applying the central portion of the hook formation to the central portion of the loop formation along the dorsum of the nose; and
   pressing the side portions of the primary component inwardly toward the sides of the nose and gradually engaging the remaining hooks and loops to produce a desired shape and restraining effect by squeezing the edema fluid from the soft tissue above the bones to be knitted together so that these bones are not splayed apart due to swelling.

7. A nasal splint kit comprising:

a primary component including a panel of manually bendable shape-retaining thin sheet material having an area in planform approximating the area of a human nose, and a first layer of thin flexible sheet material of the same planform secured to one face of the panel;

the first layer of sheet material being provided on its exposed face with a multi-element connector formation;

and a secondary component including a second layer of thin flexible sheet material having substantially the same planform as the panel and being provided on a first face with a multi-element connector formation;

the second face of the second layer being adapted to be secured to the nose of a patient;

one of said connector formations comprising a multiplicity of hooks and the other formation comprising a multiplicity of loops, and the two formations being adapted detachably engage other in facewise relation to secure the primary component to the secondary component.

8. A kit as claimed in claim 7 in which:

the planform of the components is substantially trapezoidal.

9. A kit as claimed in claim 7 in which:

the panel is formed of metallic material.

10. A kit as claimed in claim 7 in which:

the panel is formed of soft aluminum sheet having a thickness of the order of sixteen gauge.

11. A kit as claimed in claim 7 in which:

the exposed face of the panel is provided with a flesh-toned covering material.

12. A kit as claimed in claim 7 in which:

the second face of the second layer is provided with an adhesive coating.

* * * * *